United States Patent
Karami et al.

(10) Patent No.: US 10,463,864 B2
(45) Date of Patent: Nov. 5, 2019

(54) ENERGY HARVESTING FOR LEADLESS PACEMAKERS

(71) Applicants: THE REGENTS OF THE UNIVERSITY OF MICHIGAN, Ann Arbor, MI (US); The Research Foundation for the State University of New York, Amherst, NY (US)

(72) Inventors: Mohammad Amin Karami, Buffalo, NY (US); David J. Bradley, Ann Arbor, MI (US); Daniel J. Inman, Saline, MI (US); Mohammad Hossein Ansari, Amherst, NY (US)

(73) Assignees: THE REGENTS OF THE UNIVERSITY OF MICHIGAN, Ann Arbor, MI (US); The Research Foundation for the State University of New York, Amherst, NY (US)

( * ) Notice: Subject to any disclaimer, the term of this patent is extended or adjusted under 35 U.S.C. 154(b) by 253 days.

(21) Appl. No.: 15/264,657

(22) Filed: Sep. 14, 2016

(65) Prior Publication Data

US 2017/0077839 A1 Mar. 16, 2017

Related U.S. Application Data

(60) Provisional application No. 62/218,657, filed on Sep. 15, 2015.

(51) Int. Cl.
*A61N 1/375* (2006.01)
*H01L 41/113* (2006.01)
(Continued)

(52) U.S. Cl.
CPC ......... *A61N 1/3756* (2013.01); *A61N 1/3785* (2013.01); *H01L 41/1136* (2013.01); *H02N 2/186* (2013.01)

(58) Field of Classification Search
CPC ...... H02N 2/186; H02N 2/18; H01L 41/1134; H01L 41/113; A61N 1/3756; A61N 1/3787
(Continued)

(56) References Cited

U.S. PATENT DOCUMENTS 5,633,554 A * 5/1997 Kaji .................... H01L 41/0986
310/328
7,380,454 B2 * 6/2008 Dwyer ............... G01P 15/0975
73/514.16
(Continued)

FOREIGN PATENT DOCUMENTS

CN 102931878 A 2/2013
CN 103944448 A 7/2014
(Continued)

OTHER PUBLICATIONS

Ansari ("Heartbeat Energy Harvesting Using the Fan Folded. Piezoelectric Beam Geometry" proceeding of ASME 2015 International Design and engineering Technical Conference and Computers and Information in Engineering technical conference See p. 1-8 figs 1-10].*

(Continued)

*Primary Examiner* — Thomas M Dougherty
*Assistant Examiner* — Karen B Addison
(74) *Attorney, Agent, or Firm* — Harness, Dickey & Pierce, P.L.C.

(57) ABSTRACT

An energy harvester having a plurality of bimorph beams and a plurality of piezoelectric devices, wherein at least two of the piezoelectric devices are mounted to each of the plurality of bimorph beams. A plurality of rigid beams interconnect adjacent ends of the bimorph beams to define a stacked, fan-folded shape having a first end of one of the bimorph beams mounted to a structure. A tip mass is disposed on a free end of another of the plurality of bimorph beams. Upon movement of the energy harvester, the plurality of bimorph beams is caused to deflect and thereby output electrical power from the plurality of piezoelectric devices.

13 Claims, 7 Drawing Sheets

(51) Int. Cl.
*A61N 1/378* (2006.01)
*H02N 2/18* (2006.01)

(58) Field of Classification Search
USPC ............... 310/330, 370, 332, 328, 311, 339
See application file for complete search history.

(56) References Cited

U.S. PATENT DOCUMENTS

| | | | | |
|---|---|---|---|---|
| 7,439,657 | B2* | 10/2008 | Clingman | H01L 41/1134 310/332 |
| 7,948,153 | B1 | 5/2011 | Kellogg et al. | |
| 8,471,439 | B2* | 6/2013 | Moon | H01L 41/1136 310/330 |
| 8,860,553 | B2* | 10/2014 | Lal | G21H 1/02 310/311 |
| 9,294,014 | B2* | 3/2016 | Near | H01L 41/1134 |
| 9,590,533 | B2* | 3/2017 | Inman | H01L 41/1136 |
| 9,647,579 | B2* | 5/2017 | Lee | H02N 2/186 |
| 2010/0072759 | A1 | 3/2010 | Andosca et al. | |
| 2012/0068576 | A1 | 3/2012 | Lee | |
| 2013/0226260 | A1* | 8/2013 | Brenner | A61N 1/3785 607/35 |
| 2013/0293069 | A1* | 11/2013 | Sakaguchi | H02N 2/186 310/348 |
| 2014/0285067 | A1 | 9/2014 | Li et al. | |

FOREIGN PATENT DOCUMENTS

| | | |
|---|---|---|
| CN | 104283460 A | 1/2015 |
| CN | 104904110 A | 9/2015 |
| JP | 2013158117 A | 8/2013 |
| WO | 2011093179 A1 | 8/2011 |
| WO | 2014116794 A1 | 7/2014 |

OTHER PUBLICATIONS

Inman[Analytical Modeling and Experimental verification of the Vibrations of the zig zag Microstructure for Energy harvesting journal of viberation and acoustics].*
International Search Report and Written Opinion for PCT/US2016/051858, dated Dec. 23, 2016; ISA/KR.
M.H. Ansari et al. "Heartbeat Energy Harvesting Using the Fan-Folded Piezoelectric Beam Geometry", Proceedings of ASME 2015 International Design and Engineering Technical Conferences & Computers and Information in Engineering Conference, Aug. 2015, pp. 1-10.

* cited by examiner

_Fig-3_

_Fig-4_

_Fig-5A_

Frequence Spectrum of Heartbeat

ENERGY HARVESTING FOR LEADLESS PACEMAKERS

CROSS-REFERENCE TO RELATED APPLICATIONS

This application claims the benefit of U.S. Provisional Application No. 62/218,657, filed on Sep. 15, 2015. The entire disclosure of the above application is incorporated herein by reference.

FIELD

The present disclosure relates to energy harvesting for powering leadless pacemakers.

BACKGROUND AND SUMMARY

This section provides background information related to the present disclosure which is not necessarily prior art. This section provides a general summary of the disclosure, and is not a comprehensive disclosure of its full scope or all of its features.

Energy harvesting devices and their unique ability to convert the ambient energy into electrical energy have attracted much interest in industrial and manufacturing sectors. Several studies have been done in analysis and development of this technology.

Accordingly, a fan-folded piezoelectric energy harvester is designed to generate electricity using heartbeats vibration. In some embodiments, this energy harvester consists of several bimorph beams stacked on top of each other making a fan-folded shape. In some embodiments, each beam has a brass substrate and two piezoelectric patches attached on both sides of it. These beams are connected to each other by rigid beams. One end of energy harvester 10 is clamped to the wall and the other end is free to vibrate. A tip mass is placed at the free end to enhance the output power of energy harvester 10 and reduce the natural frequency of the system.

High natural frequency is one major concern about the micro-scaled energy harvesters. In some embodiments, the size for this energy harvester is 1 cm by 1 cm by 1 cm, which makes the natural frequency very high. By utilizing the fan-folded geometry and adding tip mass and link mass to the configuration, this natural frequency is reduced to the desired range.

In some embodiments, the generated electricity can be used to power a pacemaker. If enough electricity is generated, the pacemaker operates with a smaller backup battery or none at all, and the patient does not need to have a surgery every seven to ten years due to battery depletion.

Vibration is one of the common sources in energy harvesting. Some conventional sources have studied compact magnetic power generators using different sources of energy, including vibration. One commonly used method of converting vibration into electricity is by using piezoelectric materials. The piezoelectric effect converts mechanical strain into electric current or voltage. A piezoelectric material generates a small voltage whenever it is mechanically deformed. Using vibration and piezoelectric effect has been investigated by numerous groups. There were some studies on energy harvesting using vibration from flying birds or insect flights. Using the weight of passing cars or human weight is another way of generating electricity from piezoelectric beams.

There were some studies in finding the mode shapes of discontinues devices. Wickenheiser, in his research, uses transfer matrices to find the mode shapes of beam structures with pointwise discontinuities.

According to the principles of the present teachings, a new zigzag microstructure is provided that lowers the natural frequency of the system comparing to cantilevered beam. The present teachings introduce linear and nonlinear piezoelectric devices to recharge the batteries of the pacemakers continuously. Energy harvester 10 converts the vibrations from the heartbeats to electrical energy needed for powering the battery.

According to the present disclosure, a fan-folded structure is provided and studied. The free vibration modes for a seven beam structure are found. Other theoretical results were used to verify the method. A tip mass added to energy harvester 10 to decrease the natural frequency of the system and increase the output generated power was provided. The effect of the link masses is also considered in the calculation to have more accurate results. An electromechanical model for vibration and energy harvesting characteristics of energy harvester 10 is presented. The power generated from heartbeat acceleration is calculated for energy harvester 10. The generated power can be used to power a pacemaker. Although the power required for a pacemaker is very low (about 1 after few years, patients require another surgical operation to replace their pacemaker depleted battery. This energy harvester could also be built in larger scale and replace the battery in portable devices, such as cellphones or generate electricity for wireless sensors.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 2A-2D exhibit the first four modes of a seven beam energy harvester, respectively.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Device Configuration

According to the present teachings, as illustrated in FIGS. 1A-1D, a fan-folded design as the structure of an energy harvester 10. In some embodiments, energy harvester 10 can comprise a plurality of horizontal bimorph beams 12a-12n and vertical rigid beams 14. The bimorph beams 12 are connected to each other by the vertical rigid links 14. The bimorph beams 12 can comprise a spring brass layer 16 as the substrate and two piezoelectric patches 18 attached on the brass layer 16. Brass is chosen for the substrate due to its large density and relatively large Young's modulus. However, it should be understood that alternative materials may be used. When the beams 12 are deflected, electrical energy is generated by the piezoelectric layers 18. One end 20 of the design is clamped to a base structure 22 as the other end 24 is free to move. A tip mass 26 may be placed at the free end 24 of the energy harvester 10. One major advantage of using this design is the decrease in the natural frequencies of the structure without significant increase in the size of the energy harvester 10. Adding tip mass 26 and link mass 14 to the system decreases the natural frequency even more. In some embodiments, the source of the vibration of the system is heartbeat acceleration and a natural frequency under 200 Hz is a desired natural frequency for the energy harvester 10.

Energy harvester 10 consists of several uniform composite beams 12 and each beam is modeled with the Euler-Bernoulli beam theory. The structure vibrates due to base excitation. Each beam 12a can bend and deflect which changes the start position of the next beam 12b. The deflection of the beam $w_i$ is a function of the length x, and time t. The index i is the beam number (from 1 to n). The coupled mechanical equation of a beam with tip mass is:

$$\rho A \frac{\partial^2 w_{rel}}{\partial t^2} + YI \frac{\partial^4 w_{rel}}{\partial x^4} = \quad (1)$$

$$-\propto \left[ \frac{d\delta(x)}{dx} - \frac{d\delta(x-L)}{dx} \right] v(t) - \left[ \begin{array}{c} \rho A + m_l \delta(x-x^*, i-k) + \\ M_t \delta(x-x_{end}, i-n) \end{array} \right] \frac{d^2 W_b}{dt^2}$$

Where $\rho A$ is the total mass per unit length of the beam, which is a function of b (width of the beam), density of the piezoelectric and substrate ($\rho_p, \rho_s$), and their thickness ($t_p, t_s$):

$$\rho A = b(\rho_s t_s + 2\rho_p t_p) \quad (2)$$

$W_{rel}(x,t)$ is the deflection along the z-axis (FIG. 1A), YI is the equivalent bending stiffness of the composite beam. $m_l$ is the link mass and $x^*$ is 0 (if i is an odd number) or length of the beam, L, (if i is an even number). Index k is from 2 to n. $M_t$ is the tip mass and $\delta(x)$ is the Dirac delta function that satisfies:

$$\int_{-\infty}^{+\infty} \frac{d^{(n)} \delta(x-x_0)}{dx^{(n)}} f(x) dx = (-1)^n \frac{df^{(n)}(x_0)}{dx^{(n)}} \quad (3)$$

$\propto$ is the coupling term and for parallel connection:

$$\propto = -2 \int_{\frac{t_s}{2}}^{t_p + \frac{t_s}{2}} e_{31} \frac{b}{t_p} z dz = -2b e_{31} \frac{t_p + t_s}{2} \quad (4)$$

Where $e_{31}$ is the piezoelectric coefficient.

We solve the undamped, uncoupled equation to find the free vibration mode shapes. In order to find the free vibration modes, we set the left hand side of Eq. (1) to zero:

$$\rho A \frac{\partial^2 W_i}{\partial t^2} + YI \frac{\partial^4 W_i}{\partial x^4} = 0 \quad (5)$$

The solution for the free vibration can be shown as a linear combination of all natural motions of the beam (Section 11):

$$W_i(x, t) = \sum_{j=1}^{\infty} \phi_{ji}(x) T_j(t) \quad (6)$$

Where, $\emptyset_{ji}$ is the jth natural mode shape of the ith beam, and $T_j$ is the time dependent function. Substituting Eq. (6) in Eq. (5):

$$\frac{YI}{\rho A} \frac{\phi_{ji}(x)^4}{\phi_{ji}(x)} + \frac{\ddot{T}_j}{T_j} = 0 \rightarrow \frac{YI}{\rho A} \frac{\phi_{ji}(x)^4}{\phi_{ji}(x)} = \frac{\ddot{T}_j}{T_j} = -\omega_{nj}^2 \quad (7)$$

The solution can be found in the form of:

$$\phi_{ji}(x) = a_{i1} \sin\left(\frac{\beta_j}{\sqrt{C}}\right) + a_{i2} \cos\left(\frac{\beta_j}{\sqrt{C}}\right) + a_{i3} \sinh\left(\frac{\beta_j}{\sqrt{C}}\right) + a_{i4} \cosh\left(\frac{\beta_j}{\sqrt{C}}\right) \quad (8)$$

Where $a_{i1}$, $a_{i2}$, $a_{i3}$, $a_{i4}$ and $\beta_j$ are calculated using the boundary, continuity and equilibrium conditions, and C is:

$$C = \sqrt{\frac{YI}{\rho A}} \quad (9)$$

By using the above equations and considering boundary and continuity conditions, the mode shapes and natural frequencies of a fan-folded structure are derived in the next section.

Free Vibration Modes

In order to find the coefficients in Eq. (8) we use two boundary conditions at each end, zero deflection and slope at the clamped end, zero moment and force at the free end. For a fan-folded structure (FIG. 1) we have:

$$\begin{cases} \phi_{j1}(x^*_{clamped}) = 0 \\ \phi'_{j1}(x^*_{clamped}) = 0 \\ YI\phi''_{jn}(x^*_{free}) = 0 \\ YI\phi^{(3)}_{jn}(x^*_{free}) \pm M_t\omega^2_{nj}\phi_{jn}(x^*_{free}) = 0 \end{cases} \quad (10)$$

$x^*$ is zero or L (length of the beam), depending on the configuration of the fan-folded structure. The plus sign in the last equation is associated with $x_{free}^*=0$ and the minus sign is associated with $x_{free}^*=L$. $\omega_{nj}$ is the natural of the jth mode:

$$\omega_{nj} = \beta_j^2 \quad (11)$$

There are four unknown coefficients for each beam. To find these coefficients, more equations are needed. By writing the continuity and equilibrium condition at the joints where beams are connected we have four more equations for every connection:

$$\begin{cases} \phi_{ji}(x_{end}) = \phi_{j(i+1)}(x_{end}) \\ \phi'_{ji}(x_{end}) = \phi'_{j(i+1)}(x_{end}) \\ YI\phi''_{ji}(x_{end}) = -YI\phi''_{j(i+1)}(x_{end}) \\ YI\phi^{(3)}_{ji}(x_{end}) = -YI\phi^{(3)}_{j(i+1)}(x_{end}) \pm m_l\omega^2_{nj}\phi_{j(i+1)}(x_{end}) \end{cases} \quad (12)$$

Again here, the $x_{end}$ is zero or 'L' depending on the connection place. In the last equation if $x_{end}=0$ the sign of the terms associated with the link mass ($m_l$) is positive and if $x_{end}=L$ the sign is negative. Due to the small size of the structure we do not consider the effect of the moment of the link mass in the third equation. If the size increases we need to add that term to the equation. These set of equations can be written in matrix form:

$$[L_i]_{4\times 4} \begin{bmatrix} a_{i1} \\ a_{i2} \\ a_{i3} \\ a_{i4} \end{bmatrix} = [R_{i+1}]_{4\times 4} \begin{bmatrix} a_{(i+1)1} \\ a_{(i+1)2} \\ a_{(i+1)3} \\ a_{(i+1)4} \end{bmatrix} \quad (13)$$

Where $$L_i = \begin{bmatrix} \sin(q_jx^*) & \cos(q_jx^*) & \sinh(q_jx^*) & \cosh(q_jx^*) \\ \cos(q_jx^*) & -\sin(q_jx^*) & \cosh(q_jx^*) & \sinh(q_jx^*) \\ -\sin(q_jx^*) & -\cos(q_jx^*) & \sinh(q_jx^*) & \cosh(q_jx^*) \\ -q_j^3\cos(q_jx^*) & q_j^3\sin(q_jx^*) & q_j^3\cosh(q_jx^*) & q_j^3\sinh(q_jx^*) \end{bmatrix} \quad (14)$$

$$R_{i+1} = \begin{bmatrix} \sin(q_jx^*) & \cos(q_jx^*) & \sinh(q_jx^*) & \cosh(q_jx^*) \\ \cos(q_jx^*) & -\sin(q_jx^*) & \cosh(q_jx^*) & \sinh(q_jx^*) \\ \sin(q_jx^*) & \cos(q_jx^*) & -\sinh(q_jx^*) & -\cosh(q_jx^*) \\ q_j^3\cos(q_jx^*) \pm \omega^2_{nj}\frac{m_l}{YI}\sin(q_jx^*) & -q_j^3\sin(q_jx^*) \pm \omega^2_{nj}\frac{m_l}{YI}\cos(q_jx^*) & -q_j^3\cosh(q_jx^*) \pm \omega^2_{nj}\frac{m_l}{YI}\sinh(q_jx^*) & -q_j^3\sinh(q_jx^*) \pm \omega^2_{nj}\frac{m_l}{YI}\cosh(q_jx^*) \end{bmatrix} \quad (15)$$

In which $$q_j = \left(\frac{\beta_j}{\sqrt{C}}\right) \quad (16)$$

By writing Eq. (13) for all the connections we have:

$$\begin{bmatrix} a_{n1} \\ a_{n2} \\ a_{n3} \\ a_{n4} \end{bmatrix} = [R_n]^{-1}[L_{n-1}][R_{n-1}]^{-1}[L_{n-2}] \ldots [R_2]^{-1}[L_1] \begin{bmatrix} a_{11} \\ a_{12} \\ a_{13} \\ a_{14} \end{bmatrix} \quad (17)$$

Equations (10) and (17) imply that $$\begin{bmatrix} BC0_{2\times 4} \\ BCe_{2\times 4}[R_n^{-1}L_{n-1}R_{n-1}^{-1}L_{n-2} \ldots R_2^{-1}L_1]_{4\times 4} \end{bmatrix} \begin{bmatrix} a_{11} \\ a_{12} \\ a_{13} \\ a_{14} \end{bmatrix} = 0 \quad (18)$$

The matrix N accordingly is defined as:

$$N = \begin{bmatrix} BC0_{2\times 4} \\ BCe_{2\times 4}[R_n^{-1}L_{n-1}R_{n-1}^{-1}L_{n-2} \ldots R_2^{-1}L_1]_{4\times 4} \end{bmatrix}_{4\times 4} \quad (19)$$

In order to have a nontrivial solution for Eq. (18) the condition det(N)=0 must be satisfied. The values of $\omega_{nj}$ which makes this determinant zero are the natural frequencies of the structure. For finding the coefficients of the mode shapes we solve Eq. (18) for a given value of $a_{11}$. After finding the coefficients of the first beam the other beam's modes are calculated as:

$$\begin{bmatrix} a_{i1} \\ a_{i2} \\ a_{i3} \\ a_{i4} \end{bmatrix} = R_i^{-1}L_{i-1}R_{i-1}^{-1}L_{i-2} \ldots R_2^{-1}L_1 \begin{bmatrix} a_{11} \\ a_{12} \\ a_{13} \\ a_{14} \end{bmatrix} \quad (20)$$

To verify the method, two known cases of a cantilevered beam and a two member structure were compared to the results using this method. The main advantage of this method is reducing the matrix size which decreases the numerical calculation significantly. When the number of the beams increases the decrease in overall time of the calculations is considerable. Another advantage of this formulation is avoiding extremely large values of determinant which might cause numerical errors.

Solving the Governing Equations

In the configuration that we have the beams are connected electrically in parallel. Since the deflection of the beams is opposite of each other in some mode shapes, we use a switch to keep or to reverse the polarity of the generated voltage. These switches decide if the current going to each member should be added to or subtracted from the current in other members. Considering the switches and using Eq. (6) and Eq. (1), we have:

$$YI\sum_{j=1}^{\infty}T(t)_j\phi_{ji}^{(4)} + \rho A\sum_{j=1}^{\infty}\ddot{T}(t)_j\phi_{ji} = -\alpha P_i\left[\frac{d\delta(x)}{dx} - \frac{d\delta(x-L)}{dx}\right]v(t) - \quad (21)$$
$$[\rho A + \ +m_l\delta(x-x^*, i-k) \ + M_t\delta(x-x_{end}, i-n)]\ddot{W}_b$$

Where $P_i$ is the switch for the ith member and it is either 1 or $-1$. The sign of the switches for each mode is decided based on:

$$P_i=\text{Sign}(\phi_{ji}'(l)-\phi_{ji}'(0)) \quad (22)$$

The arrangement of these switches might be different for each mode, but for building energy harvester 10 one cannot change the switches during the vibration. So the states of the switches are assigned based on the dominant vibration mode. We then multiply Eq. (21) by $\phi_{ji}$ and we integrate from zero to l (length of the beam). Due to orthogonality condition:

$$YIT_j\int_0^l\phi_{ji}\phi_{ji}^{(4)}dx + \rho A\ddot{T}(t)_j\int_0^l\phi_{ji}\phi_{ji}dx = -\alpha P_i[\phi_{ji}'(l)-\phi_{ji}'(0)] \quad (23)$$
$$v(t) - \left[\rho A\int_0^l\phi_{ji}dx + m_l\phi_{jk}(x^*) + M_t\phi_{jn}(x_{end})\right]\ddot{W}_bdx$$

The mode shapes used in here are the mass normalized mode shape that satisfies:

$$\sum_{i=1}^n\rho A\int_0^l\phi_{ji}^2dx + \sum_{i=2}^n m_l\phi_{ji}^2(x^*) + M_t\phi_{jn}^2(x_{end}) = 1 \quad (24)$$

Using Eq. (7) and considering mass normalized mode shapes, we have:

$$\ddot{T}_j + \omega_{nj}^2 T_j = -\chi_j v(t) - \gamma_j \ddot{W}_b \quad (25)$$

where:

$$\chi_j = \alpha\sum_{i=1}^n P_i(\phi_{ji}'(l) - \phi_{ji}'(0)) \quad (26)$$
$$\gamma_j = \rho A\sum_{i=1}^n\int_0^l\phi_{ji}dx + +m_l\phi_{jk}(x^*) + M_t\phi_{jn}(x_{end})$$

By taking the Fourier transform of Eq. (25), we have the frequency domain equation:

$$(\omega_{nj}^2 - \omega^2)\eta_j(\omega) = -\chi_j V(\omega) - \gamma_j a_b(\omega) \quad (27)$$

In which, $\eta_j(\omega)$, $V(\omega)$, and $a_b(\omega)$ are the Fourier transforms of $T_j$, $v(t)$, and $\ddot{W}_b$. One equation is known so far, meaning another equation is needed to solve for the two unknowns, $T_j$ and $v(t)$. The equations which relate the strain and electric displacement to the stress and the electric field are the piezoelectric constitutive equations:

$$D_3 = -d_{31}Y_pS_1 - \epsilon_{33}^sE_3$$
$$T_1 = Y_p(S_1 - d_{31}E_3) \quad (28)$$

In the above equations, $T_1$ is the normal stress along the x-axis, $S_1$ is the normal strain in x-axis, $d_{31}$ is the piezoelectric coupling coefficient, $Y_p$ the Young's modulus of the piezoelectric layer, $E_3$ the electric field across the thickness of the piezo layer, $\epsilon_{33}^s$ the permittivity at constant stress, and $D_3$ the electric displacement along the thickness. Using the above equation and the Kirchhoff laws for parallel connection, we have:

$$P_iC_p\dot{v}_p + i_i(t) = -2bd_{31}Y_p\frac{t_pt_s}{2}\sum_{j=1}^{\infty}\frac{dT_j}{dt}P_i[\phi_{ji}'(l) - \phi_{ji}'(0)] \quad (29)$$

Where $i_i(t)$ is the current in each member and $C_p$ is the internal capacitance for the piezo layer:

$$C_p = 2\epsilon_{33}^s\frac{Lb}{t_p} \quad (30)$$

If we take the Fourier transform of the Eq. (29), we have:

$$j\omega C_p P_i v_p + I_i(\omega) = j\omega\sum_{j=1}^{\infty}\chi_j T_j \quad (31)$$

To have the total current, we sum the current over all the members and If we model the damping as the modal damping ($2\zeta\omega_n j\omega$) the transfer function for parallel connection resulting from Eq. (25) and Eq. (31) is:

$$v_p(\omega) = \frac{\sum_{j=1}^{\infty}\frac{j\omega\chi_j\gamma_j}{\omega_{nj}^2 + 2\zeta\omega_{nj}j\omega - \omega^2}}{\frac{1}{R} + j\omega C_p + \sum_{j=1}^{\infty}\frac{j\omega\chi_j^2}{\omega_{nj}^2 + 2\zeta\omega_{nj}j\omega - \omega^2}}a_b(\omega) \quad (32)$$

Using Eq. (32) the expression for the multi-mode power frequency response function is:

$$\frac{p(\omega)}{a_b^2(\omega)} = \frac{1}{2R}\left(\frac{\sum_{j=1}^{\infty}\frac{j\omega\chi_j\gamma_j}{\omega_{nj}^2 + 2\zeta\omega_{nj}j\omega - \omega^2}}{\frac{1}{R} + j\omega C_p + \sum_{j=1}^{\infty}\frac{j\omega\chi_j^2}{\omega_{nj}^2 + 2\zeta\omega_{nj}j\omega - \omega^2}}\right)^2 \quad (33)$$

Using the expression in Eq. (32) for voltage and replacing it in Eq. (25) the tip deflection of the structure is calculated as:

$$\frac{W_{tip}(\omega)}{a_b(\omega)} = \sum_{j=1}^{\infty}\frac{-1}{\omega_{nj}^2 + 2\zeta\omega_{nj}j\omega - \omega^2}\times \quad (34)$$
$$\left(\chi_j\frac{\sum_{j=1}^{\infty}\frac{j\omega\chi_j\gamma_j}{\omega_{nj}^2 + 2\zeta\omega_{nj}j\omega - \omega^2}}{\frac{1}{R} + j\omega C_p + \sum_{j=1}^{\infty}\frac{j\omega\chi_j^2}{\omega_{nj}^2 + 2\zeta\omega_{nj}j\omega - \omega^2}} + \gamma_j\right)W_{jn}(x_{end})$$

The relative tip acceleration to the base acceleration is:

$$\frac{a_{rel}(\omega)}{a_b(\omega)} = \frac{W_{tip}(\omega)}{a_b(\omega)} * (-\omega^2) \qquad (35)$$

Results

Figure 1A:
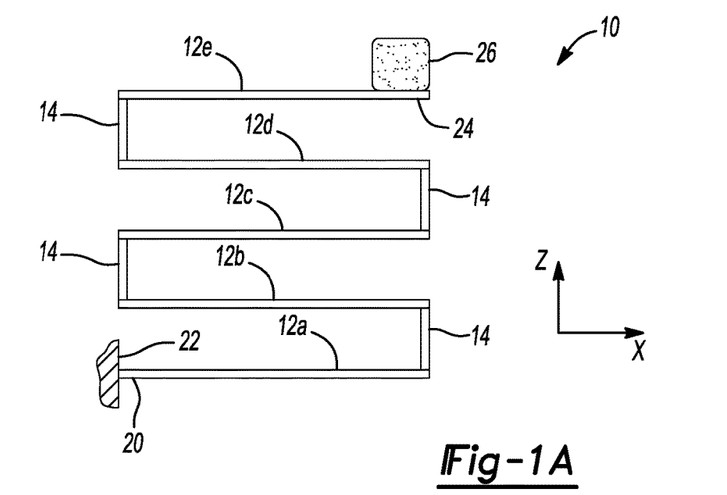
FIG. 1A is a schematic of an energy harvester with the tip mass according to the principles of the present teachings.
Figure 1B:
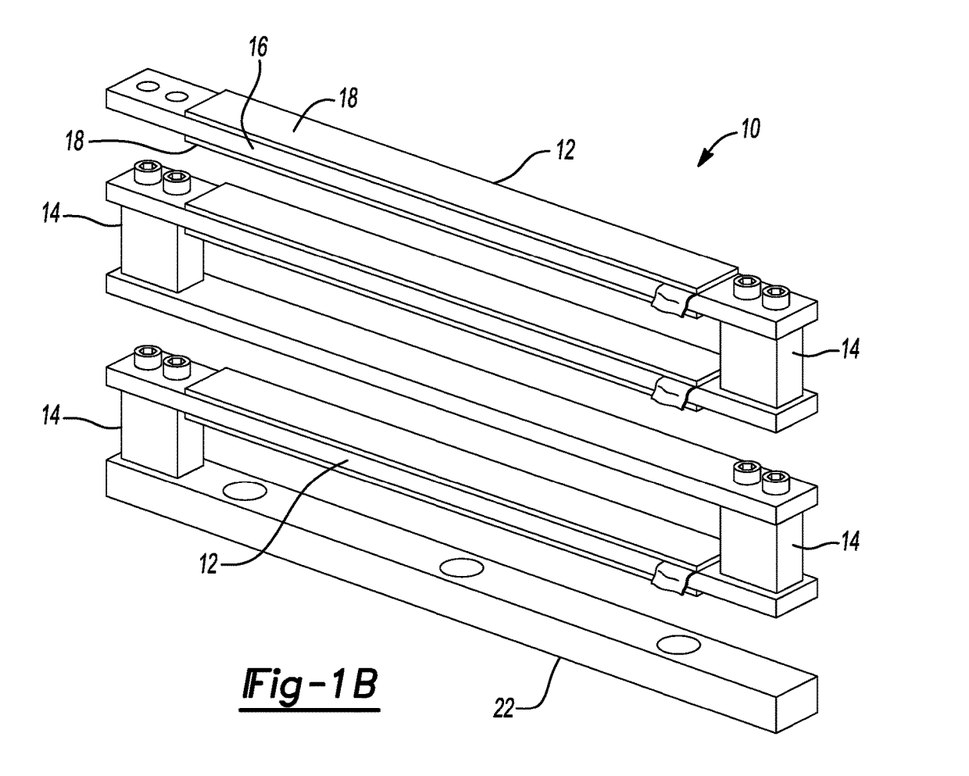
FIG. 1B is a perspective view of the energy harvester in accordance with some embodiments of the present teachings.
Figure 1C:
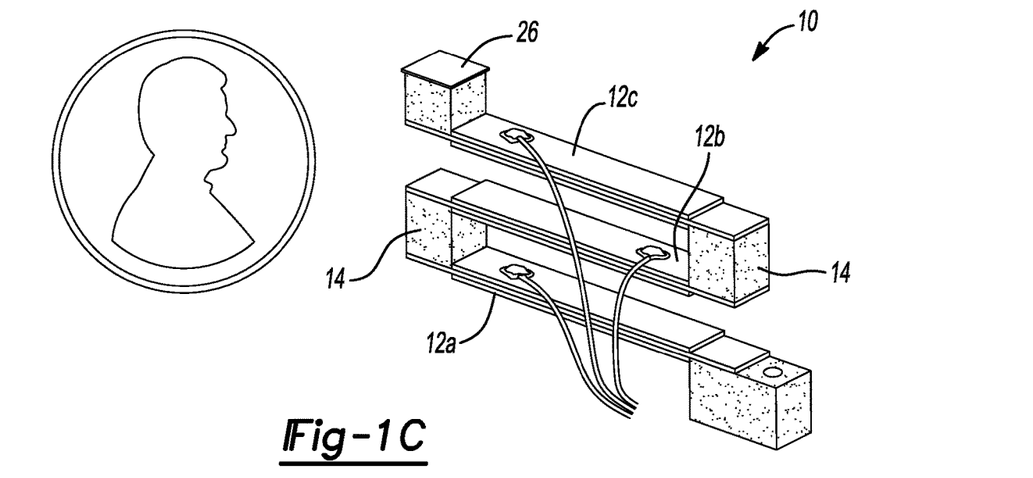
FIG. 1C is a photograph of the energy harvester in accordance with some embodiments of the present teachings.
Figure 1D:
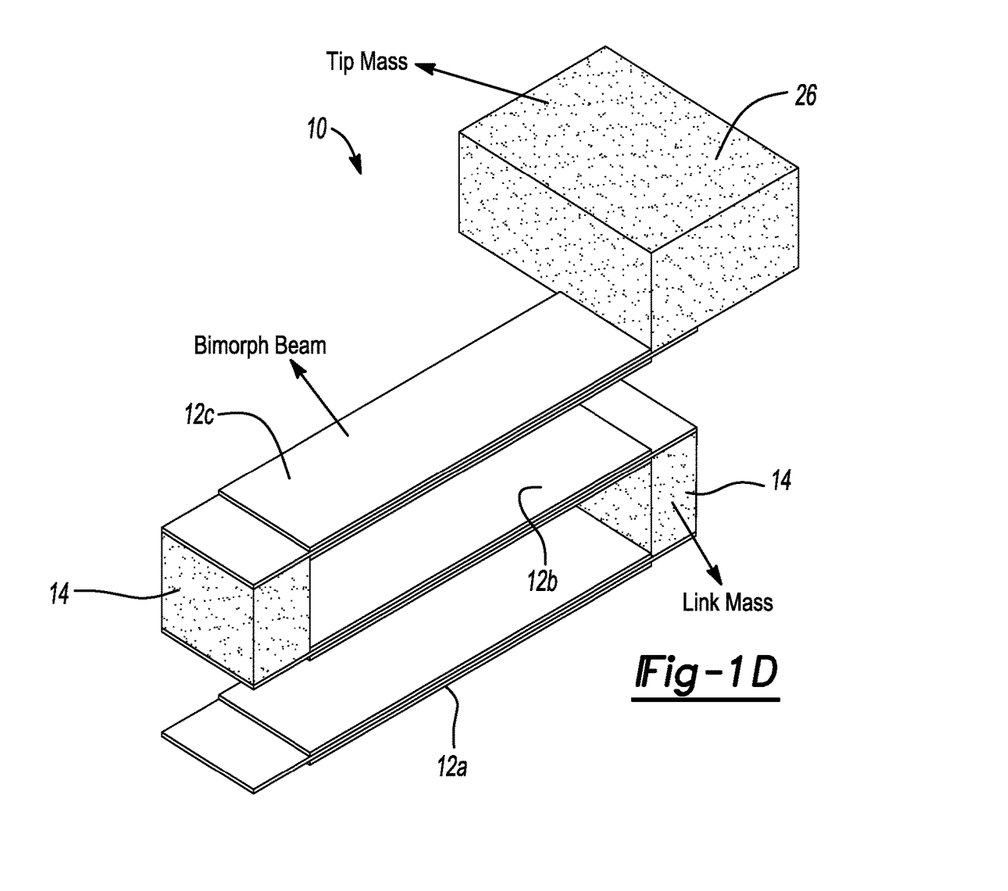
FIG. 1D is another perspective view of the energy harvester in accordance with some embodiments of the present teachings.

Accordingly, in some embodiments, energy harvester 10 can comprise seven bimorph piezoelectric beams 12 connected to each other by rigid beams 14 making a zig-zag shape. The first beam 12*a* is clamped to a wall 22 and the last beam 12*e* is free at one end 24 (FIGS. 1A and 1B). We find the free vibration modes of the configuration. Here we have the first four modes of the design. In our calculation we just consider the first natural frequency of energy harvester 10. The higher modes are not considered in our calculations due to their high natural frequency and their little effect on the final results. FIGS. 2A-2D exhibit the first four modes of a seven beam structure.

Figure 3:
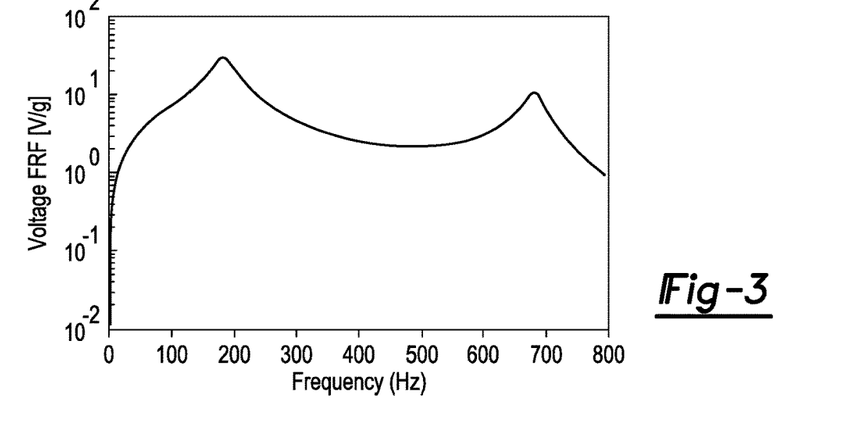
FIG. 3 is a graph illustrating output voltage versus base acceleration.

After finding the mode shapes, the frequency response function plots for a seven beam structure are generated. The structure consists of seven bimorph beams with 1 cm length and 1 cm width. PSI-5A4E PIEZO sheets from PIEZO SYSTEMS, INC. can be used as the piezoelectric element. The thickness of the brass layer and the piezoelectric layer are 0.02 and 0.01 inch. Each beam is connected to the next beam by a brass rigid beam. The length of the rigid part is 0.14 cm. The tip mass is 30 times the weight of one beam (in some embodiments, tip mass is 20 times or more the weight of one beam). A minimum safety factor of 20 is considered for energy harvester 10 to avoid fracture at where the beams are connected and where the first beam is clamped. The frequency response function of the voltage is plotted for the parallel connection of the piezoelectric layers. The voltage is proportional to the base acceleration, therefore in order to have the normalized voltage we plot the voltage per base acceleration in FIG. 3. The natural frequencies are the points where we have the maximum voltage (peaks of the plot). To maximize the output power we choose the load resistance as $$R = \frac{1}{C_p \omega_1},$$

where $\omega_1$ is the first natural frequency of energy harvester 10.

Figure 4:
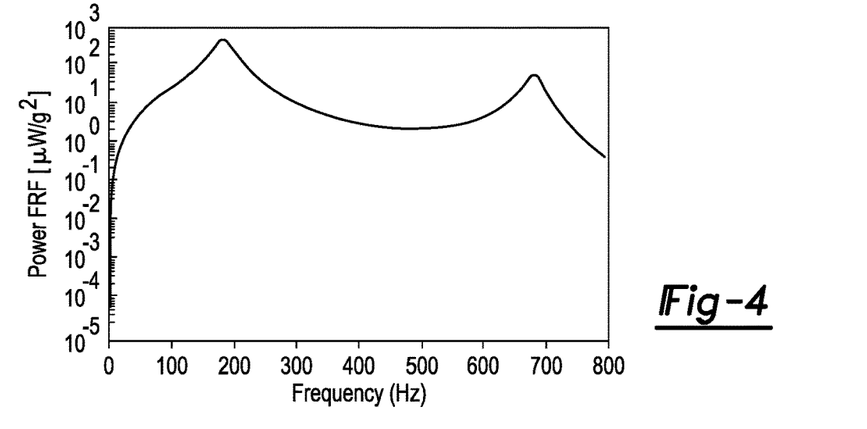
FIG. 4 is a graph illustrating the normalized power output with respect to the square of base acceleration.
Figure 5A:
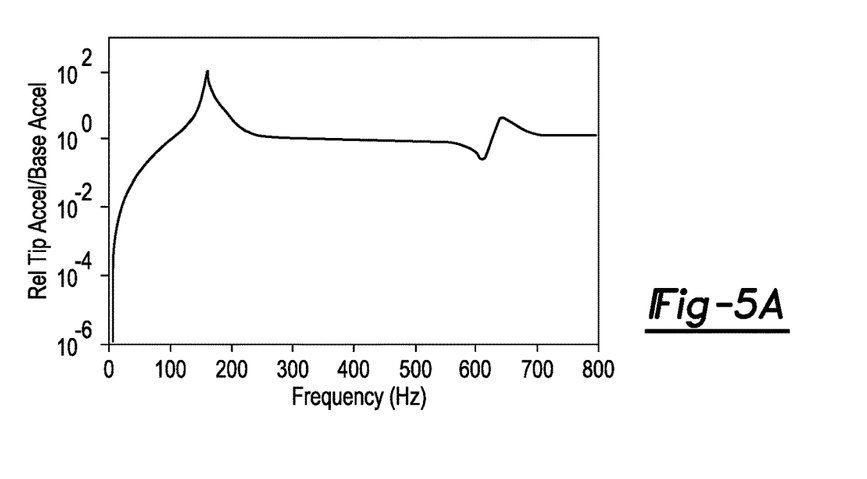
FIGS. 5A and 5B illustrate the tip relative acceleration and displacement versus the base acceleration, respectively.
Figure 5B:
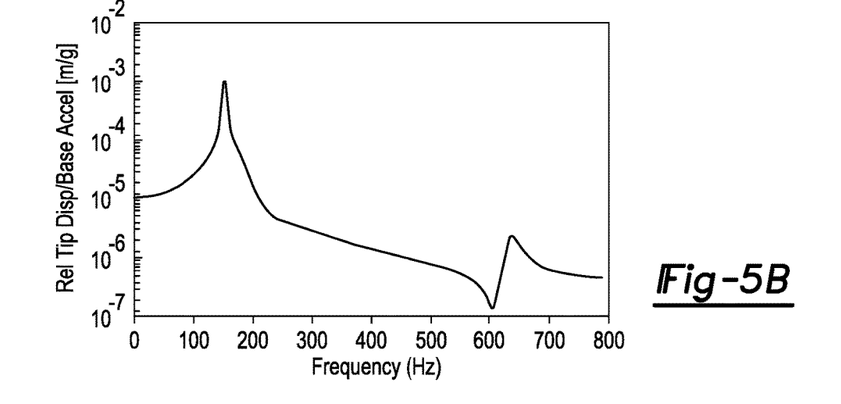

The normalized power output with respect to the square of base acceleration for a bimorph clamped free beam is illustrated in FIG. 4. As it is seen that natural frequency of energy harvester 10 are decreased significantly when they are compared to the case without tip and link masses. The first natural frequency has higher amplitude comparing to the next natural frequencies. FIGS. 5A and 5B show the tip relative acceleration and displacement to the base acceleration, respectively. The peaks in these frequency response functions are the natural frequencies of the energy harvester.

Figure 6A:
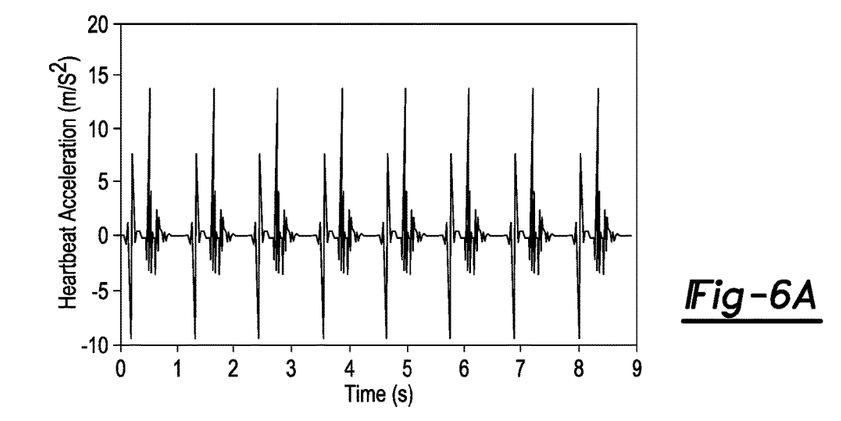
FIGS. 6A and 6B illustrate the heartbeat acceleration in time domain and frequency domain, respectively.
Figure 6B:
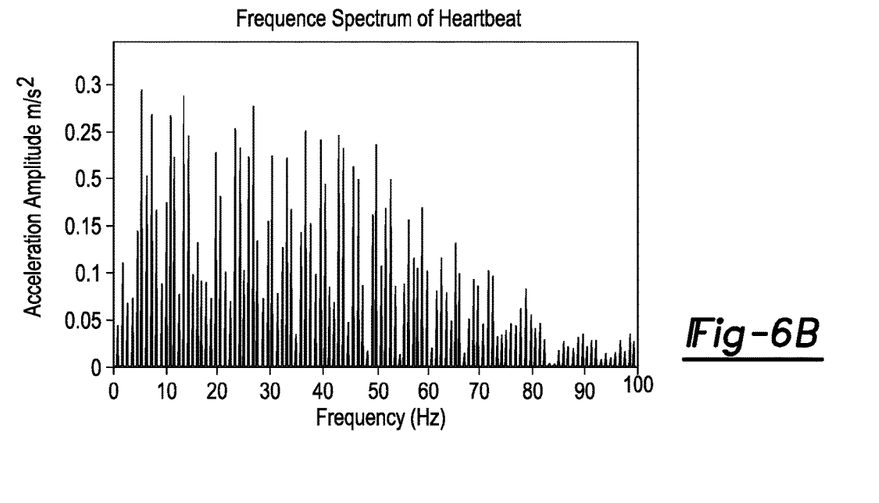

We then consider the heartbeat acceleration as the base acceleration of the system. To estimate the vibrations in the vicinity of the heart due to the heartbeat we use the ultrasonic velocity measurements performed by Kanai. FIGS. 6A and 6B show the heartbeat acceleration in time domain and frequency domain, respectively.

Figure 7:
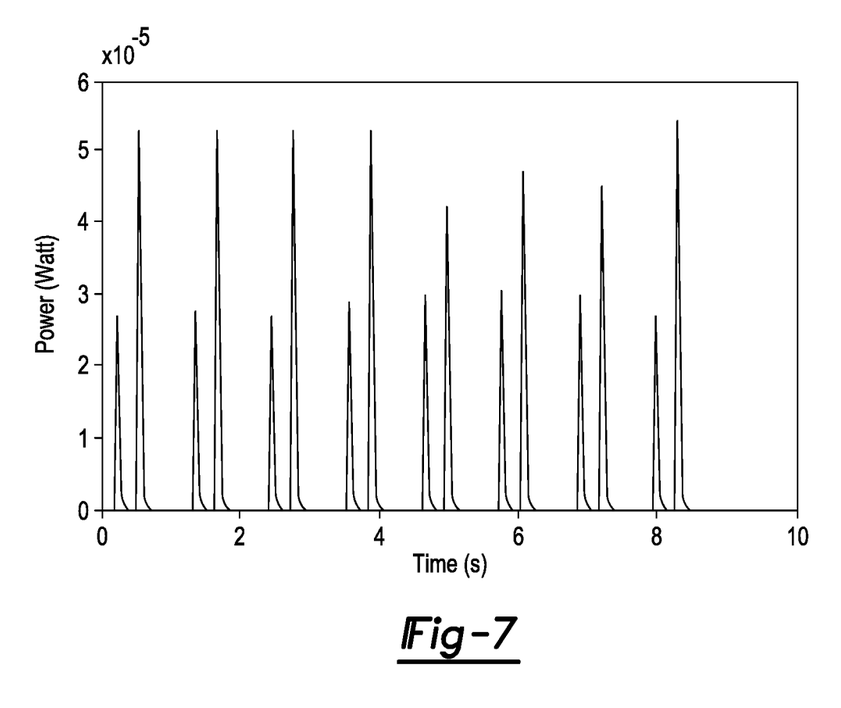
FIG. 7 is a graph illustrating the instantaneous power across a 87 kΩ purely resistive load.

Considering this base acceleration and using Eq. (32) and Eq. (33), we calculate the voltage and power generated by energy harvester 10. The time of the excitation is 9 seconds. We only consider the first natural frequency in our calculation. The next natural frequencies generated power is much less than the generated power from the first natural frequencies. The instantaneous power across a 87 kΩ purely resistive load is plotted in FIG. 7. The value of the resistive load matches the resistance having the maximum power in the first natural frequencies of energy harvester 10. The average power for generated electricity in FIG. 7 is 2.18 µW. As it mentioned the power needed for a pacemaker is less than 1 µW which shows that the generated power is sufficient for a pacemaker. In this article, the main goal is to reduce the size of the energy harvester while generating enough energy to power a pacemaker. As a result, the case presented is just a case to show that we can generate the needed power for the pacemaker while keeping the size limitations. The heartbeat spectrum in the frequency domain shows that the high amplitudes are at low frequencies (less than 50 Hz) and we can have the maximum power at 39 Hz. Author believes that by changing the tip mass and changing the beam numbers and the thickness of the beams we can reduce the first natural frequency even more and it is expected that the generated power will be increased significantly.

In this disclosure, generation of electricity from fan-folded or serpentine-shaped, bimorph piezoelectric beams with the tip mass was studied. The method for finding the mode shapes and natural frequencies of the system was explained. The boundary conditions and equilibrium and continuity conditions were discussed. For a case study, the mode shapes and natural frequencies of the configuration were calculated. The frequency response function for the voltage and power of the energy harvester were calculated and plotted. The relative tip acceleration and displacement were calculated in the frequency domain.

The electro-mechanical equations were solved for this configuration and the energy generated from 9 seconds of heartbeats was calculated. It was shown that the energy harvester generates enough energy to power a pacemaker. The fan-folded geometry and the tip mass makes it possible to have the energy harvester in small size (1 cm by 1 cm by 1 cm). Adding the tip mass reduced the natural frequency significantly. Energy harvester 10 can be implemented inside the body to generate the electricity needed for pacemakers and makes it possible to have an autonomous pacemaker without the need of a battery. The input vibrations to the energy harvester are caused by heartbeats.

The present teachings provide energy harvesting from heartbeat vibrations using fan-folded piezoelectric beams. The generated energy from the heartbeat can be used to power a leadless pacemaker. A leadless pacemaker is implanted in the heart to control abnormal heart rhythms. Unlike traditional pacemakers, leadless pacemakers do not have leads and do not need an open surgery for implantation.

The required power for a pacemaker is about 1 µW. The main obstacle for development of leadless pacemakers is the power issue. The battery takes about 60% of the size of a conventional pacemaker. The size of the conventional pacemaker batteries is too large for leadless pacemakers. The battery size issue hindered the development of leadless pacemakers for 20 years.

Recently novel batteries have been developed that make leadless pacemakers realizable. Still, the battery life is the same as traditional pacemakers and typically lasts about 6 to 7 years. Extraction of leadless pacemakers is very difficult so when the battery is depleted, a new pacemaker has to be implanted. It has been demonstrated that the principles of the present teachings generates an order of magnitude more power than the nominal power needed for a leadless pacemaker. The small size of the energy harvester and sufficient output power of energy harvester 10 are but a few of the advantages of the present invention. By way of non-limiting example, in some embodiments, the present device can be sized to about 2 cm×1 cm×0.5 cm. (1 cc in volume).

In order to utilize the 3-dimensional space available to the energy harvester, in some embodiments energy harvester 10 comprises a fan-folded design. Energy harvester 10 of the present teachings can comprise several piezoelectric beams stacked on top of each other (FIG. 1). Each beam is a bimorph piezoelectric beam, with one brass layer as the substrate and two piezoelectric layers attached on each side. The bimorph beams are connected to each other by rigid links made from platinum, for example. In some embodiments, platinum is chosen for the links due to its high density. One end of the structure is clamped as the other end is free to move.

Figure 2A:
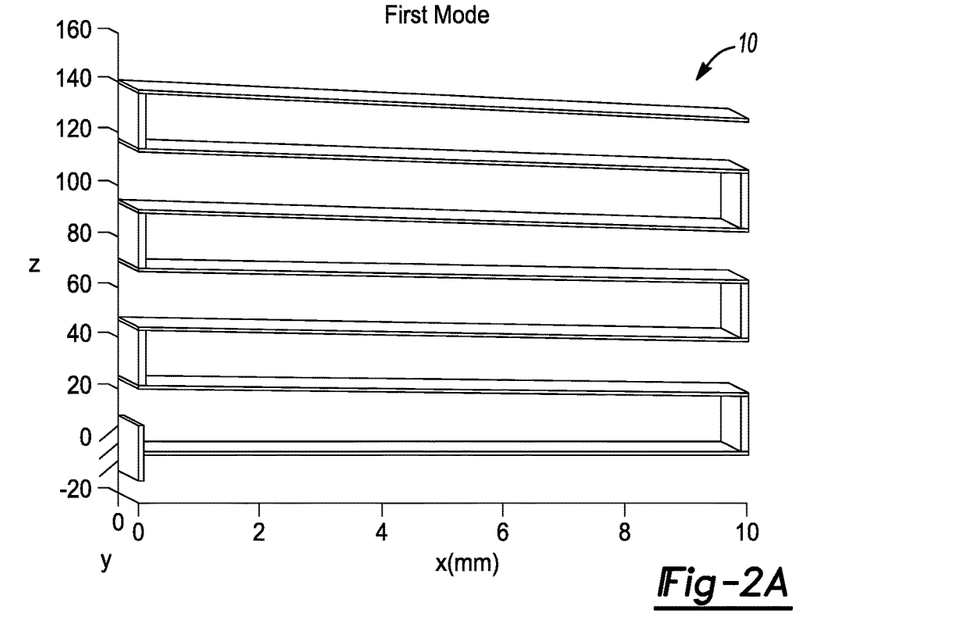

High natural frequency is one major problem in small energy harvesters. In order to generate sufficient power for a pacemaker, the first natural frequency of the energy harvester should be less than about 50 Hz. The fan-fold geometry is an effective design to reduce the natural frequency. The mass of the tip and the link can be adjusted to reduce the natural frequency. This fanfolded design makes it possible to generate more than 20 µW (more than the 1 µW required for pacemaker operations). Energy harvester 10 of the present teachings does not incorporate magnets and is thus Magnetic Resonance Imaging (MRI) compatible. Although our device is a linear energy harvester, it is shown that energy harvester 10 is relatively insensitive to the heartrate (FIG. 2.a).

Figure 2B:
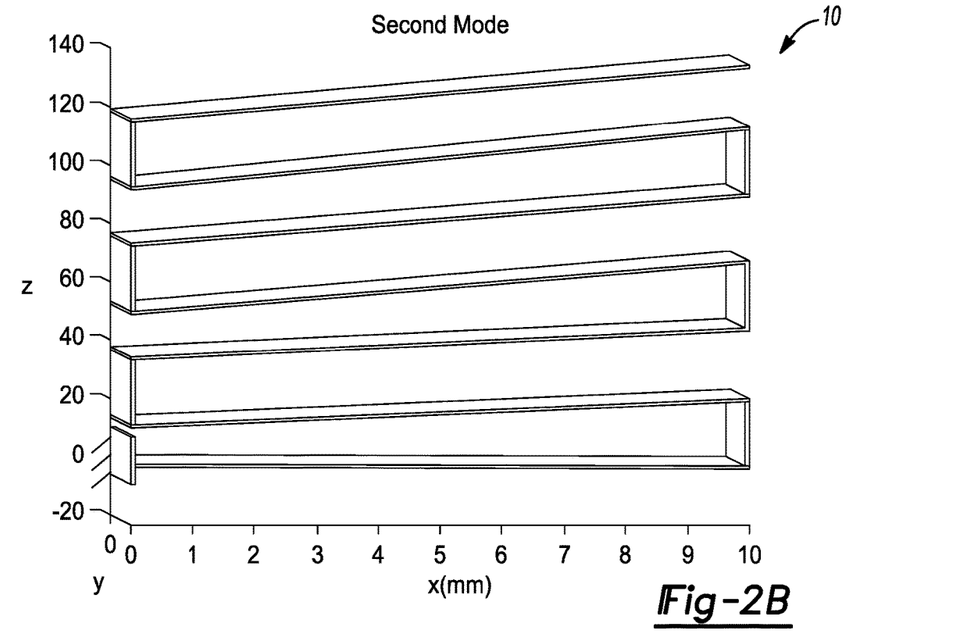
Figure 2C:
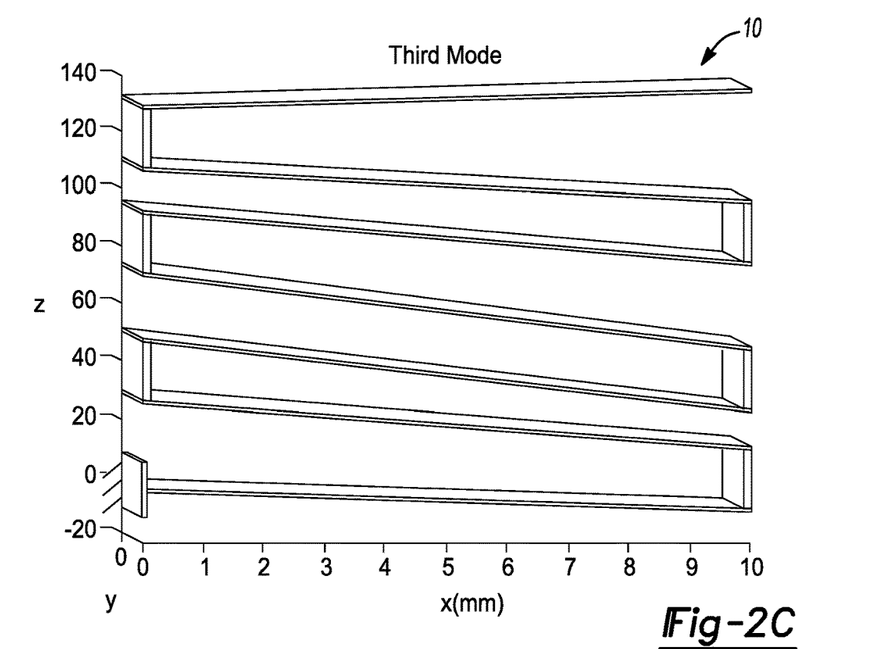
Figure 2D:
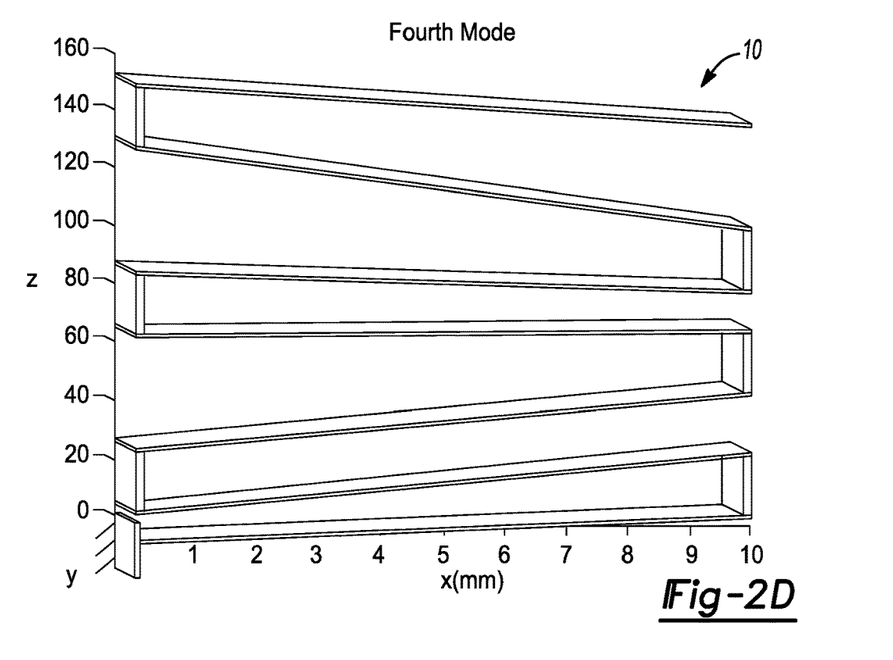

As seen in FIG. 3, the natural frequencies and the mode shapes of energy harvester 10 are calculated. The method is verified by experimental investigations (FIG. 2B). The developed analytical model is verified through comparison of theoretical and experimental voltage and tip displacement transfer functions.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An energy harvester comprising:
a plurality of bimorph beams;
a plurality of piezoelectric devices, at least two of said plurality of piezoelectric devices being mounted to each of said plurality of bimorph beams;
a plurality of rigid beams interconnecting adjacent ends of said plurality of bimorph beams to define a stacked, fan-folded shape having a first end of one of said plurality of bimorph beams being mounted to a structure; and
a tip mass being disposed on a free end of another of said plurality of bimorph beams,
wherein upon movement of the energy harvester, said plurality of bimorph beams are caused to deflect and output electrical power from said plurality of piezoelectric devices.

2. The energy harvester according to claim 1 wherein each of said plurality of bimorph beams comprises a brass substrate and said piezoelectric device is mounted thereto.

3. The energy harvester according to claim 1 wherein said at least two of said plurality of piezoelectric devices being mounted to each of said plurality of bimorph beams on opposing sides of said bimorph beam.

4. The energy harvester according to claim 1 wherein said tip mass is chosen to tune a natural frequency of the energy harvester to a desired frequency.

5. The energy harvester according to claim 1 wherein said tip mass is chosen to tune a natural frequency of the energy harvester to a frequency under 200 Hz.

6. The energy harvester according to claim 1 wherein said movement of the energy harvester is caused by a human heartbeat.

7. The energy harvester according to claim 1 wherein a weight of said tip mass is greater than 20 times the weight of one of said plurality of bimorph beams.

8. An energy harvester comprising:
a plurality of bimorph beams each having a first end and a second end;
a plurality of piezoelectric devices, at least two of said plurality of piezoelectric devices being mounted to opposing sides of each of said plurality of bimorph beams;
a plurality of rigid beams interconnecting adjacent ends of said plurality of bimorph beams to define a stacked, serpentine shape having said first end of one of said plurality of bimorph beams being mounted to a structure and said second end of said one of said plurality of bimorph beams being mounted to said first end of a second of said plurality of bimorph beams via one of said plurality of rigid beams; and
a tip mass being disposed on a free end of a last of said plurality of bimorph beams,
wherein upon movement of the energy harvester, said plurality of bimorph beams are caused to deflect and output electrical power from said plurality of piezoelectric devices.

9. The energy harvester according to claim 8 wherein each of said plurality of bimorph beams comprises a brass substrate and said piezoelectric device is mounted thereto.

10. The energy harvester according to claim 8 wherein said tip mass is chosen to tune a natural frequency of the energy harvester to a desired frequency.

11. The energy harvester according to claim 8 wherein said tip mass is chosen to tune a natural frequency of the energy harvester to a frequency under 200 Hz.

12. The energy harvester according to claim 8 wherein said movement of the energy harvester is caused by a human heartbeat.

13. The energy harvester according to claim 8 wherein a weight of said tip mass is greater than 20 times the weight of one of said plurality of bimorph beams.

* * * * *